Dec. 17, 1974 K. K. MESERVE Plant Pat. 3,662
ILEX BLUE ANGEL
Filed Aug. 9, 1973
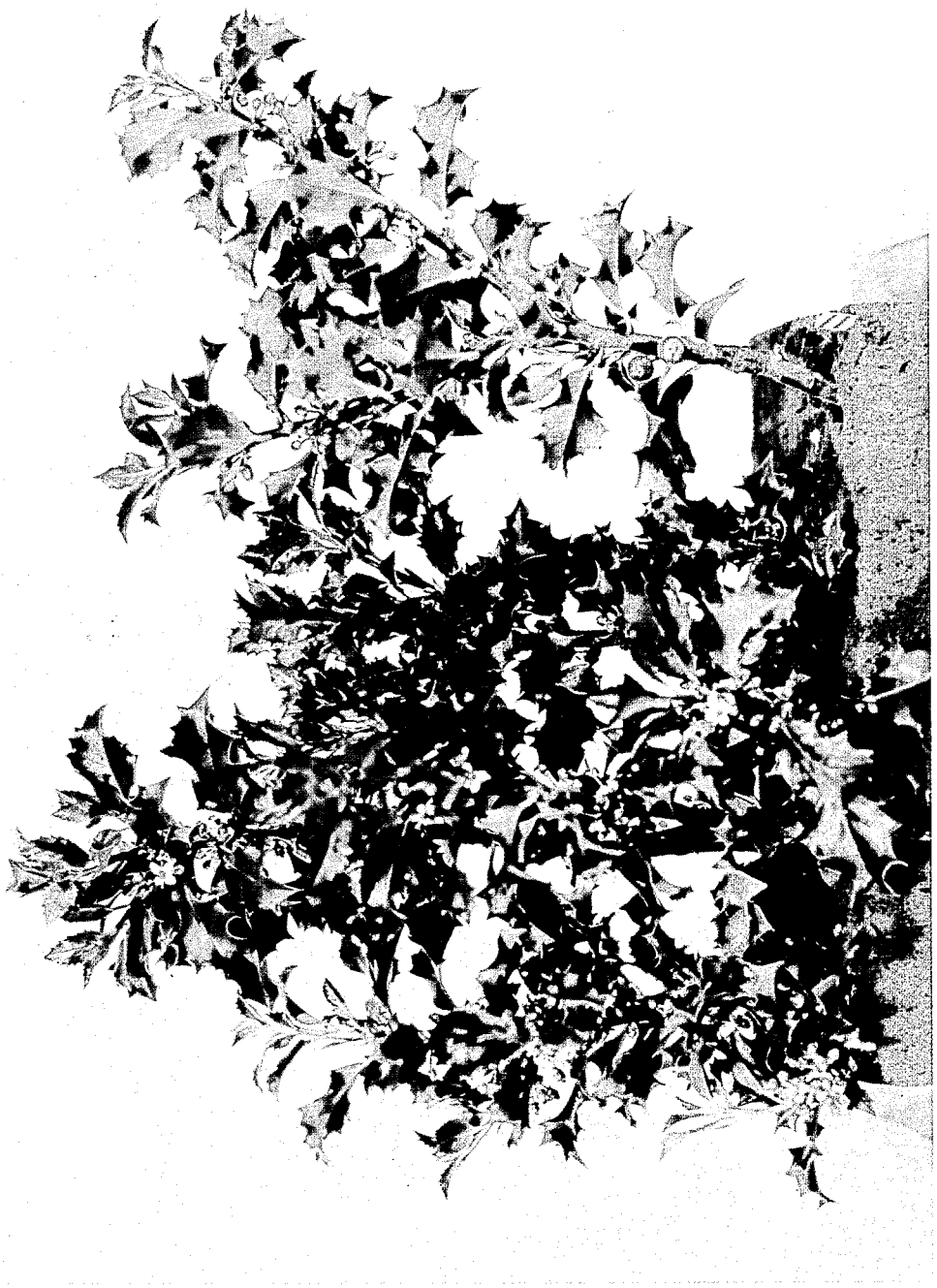

United States Patent Office

Plant Pat. 3,662
Patented Dec. 17, 1974

3,662

ILEX BLUE ANGEL

Kathleen K. Meserve, St. James, N.Y., assignor to
The Conard-Pyle Company, West Grove, Pa.

Filed Aug. 9, 1973, Ser. No. 387,042
Int. Cl. A01h 5/00
U.S. Cl. Plt.—65 1 Claim

ABSTRACT OF THE DISCLOSURE

A new and distinct variety of Ilex which was originated by crossing a seedling obtained by crossing *Ilex aquifolium* with *Ilex rugosa,* and which seedling was crossed with an unpatented and unnamed selection of *Ilex aquifolium.*

SUMMARY OF THE INVENTION

The present invention relates to a new and distinct variety of Ilex which was originated by me by crossing a seedling, whose parentage is *Ilex aquifolium* × *Ilex rugosa,* and which seedling was crossed with an unpatented and unnamed selection of *Ilex aquifolium.*

The obsectives of my breeding were to produce a new Ilex with "Christmas Holly" foliage but of more compact form and a slower rate of growth than *Ilex aquifolium* and particularly suited to contemporary landscape design requirements and environmental needs in a plant of year around ornamental value.

As a result of this breeding, I have produced a new, distinct and useful Ilex variety fulfilling my objectives and which is distinguished from its parents and all other varieties of which I am aware, as evidenced by the following unique combination of characteristics which are outstanding therein:

1. Freely branched to quickly form a compact, attractive habit of growth;
2. Abundant foliage of deep glossy green color with wavy, crinkled margins;
3. Foliage of a form distinct from any other Ilex of which I am aware. It is more glossy than *Ilex opaca* "Maurice River" and *Ilex opaca* "Menantico";
4. Moderately floriferous and producing some abortive flowers;
5. Fruit of dark red color borne in moderate quantities;
6. Winter tolerant with little or no injury east of the Mississippi River in Zone 5b of the Plant Hardiness Zone Map, Miscellaneous Publication No. 814, Revised 1965, where *Ilex opaca* is listed as hardy only to Zone 6 and *Ilex aquifolium* is listed as hardy only to Zone 7. Root hardiness superior to *Ilex crenata compacta,* Ilex × "Nellie Stevens," Ilex × "Dr. Kassab," *Ilex crenata* "Helleri," *Ilex crenata* "Hetzi," *Ilex crenata* "National," *Ilex crenata* "Compacta," *Ilex crenata* "Buxifolia," *Ilex opaca* "New Jersey Special," Ilex × "Lydia Morris," Ilex × "Edward T. Stevens," Ilex × "John Morris," *Ilex cornuta* "National," *Ilex aquifolium* "New York Botanic Garden #2" all of which died except "New York Botanic Garden #2," which was seriously injured but was not killed when overwintered in containers above ground at West Grove, Pa., while my present invention survived without injury. More cold tolerant at St. James, N.Y., where *Ilex aquifolium* varieties "Essen," "Firecracker," "Brownell Special," "Everett" and "New York Botanic Garden #2" have been injured or killed.
7. Well suited to environmental demands for ornamental plants of year around decorative value under a wide range of climatic and design conditions and which have ecological value;
8. Particularly adapted to shearing and trimming to fit contemporary landscape design where compact, hardy, attractive broadleafed evergreen plants are needed; and 9. Leaves and branches of such color tones as to give the plant an overall bluish cast.

When compared to its seed parent, my new variety has more compact, freely branched growth covered more densely with leaves having a wavy and crinkled margin of "Christmas Holly" type and produces fewer berries of deeper color.

As compared to its pollen parent, my new variety has more leaves of darker color and produced more abundantly, about ⅔ the size of its parent, with stiff, straight branches of dark color.

Asexual reproduction of my new variety by cuttings has been accomplished at St. James, N.Y., and at West Grove, Pa., and shows that its distinguishing characteristics are fixed and stable and are transmitted through succeeding propagations.

BRIEF DESCRIPTION OF DRAWING

The accompanying drawing shows typical specimens of my new variety of plant, some with flowers, and as depicted in color as nearly true as is reasonably possible to make the same in a color illustration of this character.

DETAILED DESCRIPTION OF DISCLOSURE

The following is a detailed description of my new variety, with color terminology in accordance with the Royal Horticultural Society Colour Chart of The Royal Horticultural Society, London, England:

Type: Hardy outdoor shrub, seedling, for garden decoration and ornamental landscape plantings.

Parentage: (*Ilex aquifolium* × *Ilex rugosa*) × *Ilex aquifolium.* Parents of the first cross were unamed selections of *Ilex aquifolium* and *Ilex rugosa.* Cross made in May 1958; seed sown on Sept. 28, 1958; germination in April 1960; selection made in 1963.

Locality where grown and observed: St. James, N.Y., and West Grove, Pa.

Propagation: It does hold its distinguishing characteristics through succeeding propagations by cuttings.

Flowers: Pistillate flowers are borne several to the stem in rounded clusters, on strong, short stems. Flowers are borne freely outdoors.

*Bud.*—Flowers are carried on a short, medium heavy, stiff peduncle whose color is green, Group 146D. Buds are small and globular. As calyx breaks, the color is 54C. As the first petals open, it is small, globular with color 56D on the outside margins and 56D on the inner petal area. It does open well.

*Blooms.*—Blooms are small, opening to 6.25 mm. across. Petalage is single—4 and occasionally 5 petals. Form is cupped at first, becoming very flat; petals remaining at first loosely cupped inward; becoming later at maturity loosely rolled outward. Petals are thin and soft; with inside and outside satiny. Petals are ovate.

This description of a flower was made from a plant grown outdoors in May 1972, at West Grove, Pa.:

*Color.*—Outside Surface: Color Group 56D. Inside Surface: Color Group 56D, shaded with 54D.

Flowers last 1 to 2 days, on the bush in May.

Reproductive organs:

*Pistils.*—4.

*Styles.*—Even, long, separated, of Color Group 56D.

*Stigma.*—White with 150D.

*Ovaries.*—All protruding from receptacle, Color Group 143A.

*Fruit.*—Round, 8 mm. to 12 mm. in diameter in loose clusters on short, medium heavy, stiff stems from 7 mm. to 9 mm. in length and color dull 46B. Berries are satiny and of Color Group 46A.

*Seeds.*—Few, of medium size.

Foliage:

*Leaves.*—Lanceolate, with apex and base acute and dentate.

*Foliage Size.*—Measurements taken from a random sampling of mature leaves growing midway along stems or midway between secondary branches. Measurements to tips of spines. Length; from 3.3 mm. to 4.4 mm., with an arithmetical average of 3.9 mm. Width; from 2.0 mm. to 3.4 mm., with an arithmetical average of 2.7 mm. Petiole length; from 0.4 mm. to 0.6 mm., with an arithmetical average of 5.1 mm. Spines occurred from 11 to 22 per leaf with an arithmetical average of 14.6 mm.

*Foliage Color (Mature near terminal end of branch).*—Upper surface: Very glossy, Color Group 200A. Lower surface: Dull, Color Group 148A.

*Foliage Color (Small stems from inside of plants).*—Upper surface: Bright, Color Group 147A. Lower surface: Dull, Color Group 147B.

*Foliage Color (Mature near end of branches where attached to another branch).*—Upper surface: Very glossy, Color Group 200A. Lower surface: Dull, Color Group 146A.

*Foliage Color (Young Immature Leaves).*—Upper surface: Color Group 146A with edges of Color Group 200D. Under surface: Color Group 147B, shade wtih Color Group 200D with edges of Color Group 200D.

*Stems.*—Both old and young canes: From top to bottom, dull, Color Group 200A. Heavy canes have diamond shaped spots on lower part of canes, Color Group 201B. New shoots, dull, Color Group 148A, maturing to Color Group 200B in autumn.

*Berries.*—Dark, Color Group 46A. Short stem on berries, dull, Color Group 46B.

I claim:

1. A new and distinct variety of Ilex plant, substantially as herein shown and described, characterized particularly as to novelty by the unique combination of a compact, densely branched, dwarf and vigorous growth habit, an abundance of distinctive, glossy, evergreen leaves of "Christmas Holly" type, with coarse, spiny teeth and wavy, crinkled margin, and more cold tolerant than other red berried, evergreen Ilex, with such glossy, attractive leaves and with stem and leaf color giving an overall bluish effect and bearing dark red berries of good size and having year around ornamental value particularly appropriate to landscape and environmental needs.

References Cited

UNITED STATES PATENTS

P.P. 2,434 8/1964 Meserve ---------- Plants—65

ROBERT E. BAGWILL, Primary Examiner